(12) United States Patent
Rich

(10) Patent No.: US 8,291,778 B2
(45) Date of Patent: Oct. 23, 2012

(54) EXTRACTIVE SAMPLING SYSTEM FOR FLUIDS

(76) Inventor: Ronald Rockwell Rich, Edina, MN (US)

(*) Notice: Subject to any disclaimer, the term of this patent is extended or adjusted under 35 U.S.C. 154(b) by 480 days.

(21) Appl. No.: 11/851,712

(22) Filed: Sep. 7, 2007

(65) Prior Publication Data

US 2008/0060459 A1  Mar. 13, 2008

Related U.S. Application Data

(60) Provisional application No. 60/843,317, filed on Sep. 8, 2006.

(51) Int. Cl.
*G01N 1/22* (2006.01)
(52) U.S. Cl. .................................... 73/863.23
(58) Field of Classification Search .................. None
See application file for complete search history.

(56) References Cited

U.S. PATENT DOCUMENTS

| | | | | | |
|---|---|---|---|---|---|
| 2,030,682 | A | * | 2/1936 | Campbell | 73/863.23 |
| 3,457,787 | A | * | 7/1969 | Maatsch et al. | 73/863.02 |
| 3,918,913 | A | * | 11/1975 | Stevenson et al. | 73/863.72 |
| 4,090,392 | A | * | 5/1978 | Smith et al. | 73/863.23 |
| 4,497,214 | A | * | 2/1985 | Ramelot | 73/863.12 |
| 4,594,902 | A | * | 6/1986 | Compton et al. | 73/863.23 |
| 4,974,455 | A | * | 12/1990 | McGowan et al. | 73/863.12 |
| 5,423,228 | A | * | 6/1995 | Budd et al. | 73/863.21 |
| 5,635,652 | A | * | 6/1997 | Beaudin | 73/863.03 |
| 5,777,241 | A | * | 7/1998 | Evenson | 73/863.11 |
| 5,816,701 | A | * | 10/1998 | Martin et al. | 366/208 |
| 5,999,257 | A | * | 12/1999 | Myers et al. | 356/336 |
| 6,076,410 | A | * | 6/2000 | Renslow | 73/864.34 |
| 6,425,297 | B1 | * | 7/2002 | Sharp | 73/863.33 |
| 7,434,483 | B2 | * | 10/2008 | Cueni et al. | 73/864 |
| 2002/0134174 | A1 | * | 9/2002 | Silvis et al. | 73/863.81 |
| 2003/0121336 | A1 | * | 7/2003 | Hubbell et al. | 73/863.23 |
| 2006/0288805 | A1 | * | 12/2006 | Das et al. | 73/866 |

* cited by examiner

*Primary Examiner* — Robert R Raevis
(74) *Attorney, Agent, or Firm* — Benjamin C. Armitage; Clise, Billion & Cyr, P.A.

(57) ABSTRACT

Disclosed is an extractive sampling system to secure representative fluid samples and transport to analyzers as a sample destination. The invention is directed to modification of sample acquisition components and the addition of elements to overcome sample obtainment issues that occur in a variety of fluids to be samples.

16 Claims, 3 Drawing Sheets

EXTRACTIVE SAMPLING SYSTEM FOR FLUIDS

CROSS-REFERENCE TO RELATED APPLICATIONS

This application claims the benefit of provisional patent application No. 60/843,317, filed Sep. 8, 2006, which is hereby incorporated by reference herein in its entirety.

BACKGROUND OF THE INVENTION

The present invention relates generally to fluid sampling systems either employing an analyzer selectively coupled to a sample location of a fluid for extracting a fluid sample therefrom, or alternatively for collection of a sample for subsequent analysis by an analyzer at a remote location.

1. Technical Field

Most gas and liquid chemical composition and physical property analyzers need to extract fluid samples, either continuously or intermittently, from the location where the fluid to be tested resides (the "sample location"—Si in the Figures). This sample fluid is then transported to the inside of the analyzer detector to obtain a desired test result or to a storage vessel from which sampling later occurs using another extractive sampling system. For the purposes of this disclosure, either the detector or the storage vessel constitutes a "sample destination".

2. Description of Prior Art

A variety of extractive sampling systems exist. The simplest consist of a fluid transport tube of varying diameters and lengths with or without an in-line sample pump that moves the fluid from the sample location to the sample destination. Simple fluid sampling systems are reliable and allow accurate fluid properties analysis only if the fluid is very clean, the fluid has physical and chemical properties that do not change during transport in the sampling system, the sampling is not continuous, and no valves or other flow control components are present in the flow path. Most useful sampling system applications require additional components or they will plug in a short time or damage the analyzer or flow control components.

If the fluid contains suspended solid matter, and the solid material either obstructs the flow of the fluid or interferes in some way with the pump, connecting valve, or the analyzer detector, a particle filter is often installed in or near the sample location end of the fluid transport tube. Typical sample fluid transport tube diameters on the sample location side (upstream) of the filter are 0.25 inches or greater and inside diameters are 0.18 inches or greater to increase the time before such particles obstruct the fluid transport tube and reduce sample flow. If the fluid transport tube is easily plugged by particles, a conventional remedy is to increase the cross sectional diameter of the fluid transport tube and the filter. This increase allows more solid matter to accumulate before the sampling system must be cleaned. However, the volume increase this causes slows the transit time of the sample. To compensate for this delay, a higher capacity pumping system is usually added.

Use of conventional diameter sample fluid transport tubing also constrains a sampling system in two other ways. First, if gases or liquids are sampled from furnaces or other hot sources, they must be cooled prior to entry into the analyzer. The more rapidly the fluid is cooled, the less time is involved for reactions to take place that could change the composition of the fluid. For example, when carbon monoxide gas is extracted from an ambient pressure furnace at temperatures higher than approximately 1300 Deg. F., and then is cooled in or by the sampling system to below approximately 700 Deg. F., some of the carbon monoxide reacts with itself to form carbon dioxide and carbon (as soot). The slower the cooling takes place, the greater is the conversion. Because the unit fluid transport tubing wall surface area to internal cross-sectional volume of small diameter is greater than larger diameter fluid transport tubing, fluids in small diameter fluid transport tubes cool more rapidly than those in larger diameter fluid transport tubes. The result is a more accurate chemical analysis of the sample being extracted. Also, quicker cooling deposits less of a material (like soot) that is forms in the fluid transport tube during cooling. Second, assuming a constant fluid sample velocity, smaller diameter fluid transport tubing allows less gas to be removed for analysis. In processes that use or generate small gas volumes (such as research bioprocess reactors or vacuum furnaces), this feature is important.

Regardless of sample fluid transport tube diameter, in cases where large solids or particulates can plug the sample line or the filter in an unacceptably short time, additional components are often added to the sampling system. Most often, these components periodically reverse sample flow or reverse flow ("blow back") a non-reactive usually inert clean fluid different from the sampled fluid in an attempt to remove accumulated particles from the unfiltered portion of the sample fluid transport tube and the filter itself. When a sample system that uses periodically reversing flow also includes multiple sample locations supplying a single analyzer, a second pump ("purge pump") is sometimes used to draw fresh sample into fluid transport tubing and filters prior to analysis. This pump adds to the total sample flow through each line and can accelerate sample line plugging.

In many cases, more even more complex sampling systems are employed. When some or all of the fluid can: 1, change phase (if a gas, change into a liquid and if a liquid change into a solid); 2, react in the fluid transport tube to become viscous or form a solid; or 3, if the entrained solid particles are the constituent to be analyzed, the fluid transport tubing can be heated to prevent reactions or condensation or a fluid diluent can be added at or near the sample location. While both these approaches can function with certain fluids, their addition to the sampling system adds considerable complexity and expense to the system cost and they are employed only when necessary.

None of these known fluid sample systems and enhancements can properly handle some types of fluids that are useful to measure. If the fluid contains complex mixtures of chemicals and particles that interact, change phase, are withdrawn from high temperature or high pressure sample location or if complex chemical interactions occur in the sampling system, extractive sampling systems are often unreliable and ineffective. Some examples of such complex mixtures include: combustion gases, especially those produced by burning coal; industrial gas mixtures used for metal refining, processing and treating; certain chemical manufacturing and petroleum refining processes; gases and liquids from bioprocess fermentation and cell culturing; and almost all unfiltered air and wastewater emissions. Useful analytical information that can significantly improve manufacturing processes, reduce energy use and improve environmental compliance is lost when complex fluids affect the sampling system.

As an example, the complex composition of coal combustion gas is known to require several existing extractive sampling system enhancement combinations. Even with the enhancements, they are considered unreliable and are rarely used for continuous analysis.

FIG. 1 presents a diagram of a chemical analyzer with a typical current practice sampling system for measuring the chemical composition of coal combustion products. A typical combination includes: 1, heated sample fluid transport tubing UT1-UT8, each having a respective length, LUi, or gas dilution (not shown); 2, corresponding sample particle filters FS1-FS8, associated with each of the inlet sample fluid transport tubing lines, UT1-UT8, respectively, placed near the sample location to keep the majority of the sample line free from such particles; and 3, periodic gas blow back using clean and dried air or nitrogen to dislodge accumulated sample particles including Fluid 1 Supply 101, Filter FF1 106, and Purge Valves VP1. The outlet side of the sample particle filters FSi is coupled to the common gas analyzer 110 through a respective down stream fluid transport tubing DT1-DT8, each having a respective length, LDi, and a respective series of valves including the Purge Valves VPi, the Sample select valves VSi, and Sample Flow Regulation Valve VFS, 112

For process control, automatic and continuous analyzer operation using corresponding valves, VS1-VS8, to sequentially select several sample locations is typically desired (also shown in FIG. 1). For industrial applications such a system should operate at least six months without servicing or they are considered "unreliable". However, using current practice sample system enhancements, sample system operation in a coal-fired power plant typically requires weekly service to prevent plugging. Attempts to improve sample system life by increasing the sample line cross-section and the sample flow rate may or may not extend sampling system operating time, however plugging still occurs in much less than 6 months and do to slower cooling, analysis samples from hot locations may become less accurate.

The reduced time before plugging in this and similar applications is caused by at least three properties of the sampled gas. First, the density of solid particles is very high and their size very small which allows them to be effectively entrained in the sample gas. These particles rapidly fill the portion of the sampling system fluid transport tubing LUi upstream of the filter and rapidly accumulate on the filter itself.

Second, coal combustion gas contains a significant portion of condensable chemicals that are in vapor phase in the combustion gas but partially condense even when sample systems are heated to high temperatures or dilution systems are used. The condensables tend to coat the inside diameter of the sample lines upstream of the filter (in combination with the particles present) and progressively decrease the remaining inside diameter reducing sample gas flow. Many of the condensables are very viscous and difficult to remove by blow back.

Third, the condensed liquids and the deposited particles inside the fluid transport tubes chemically react at the points of temperature transition and form a solid cement-like material that adheres to the inside sample fluid transport tube wall and filter. The combination of the condensables' viscosity and there reactions render gas blow back ineffective.

DETAILED DESCRIPTION OF THE INVENTION

Figure 1:
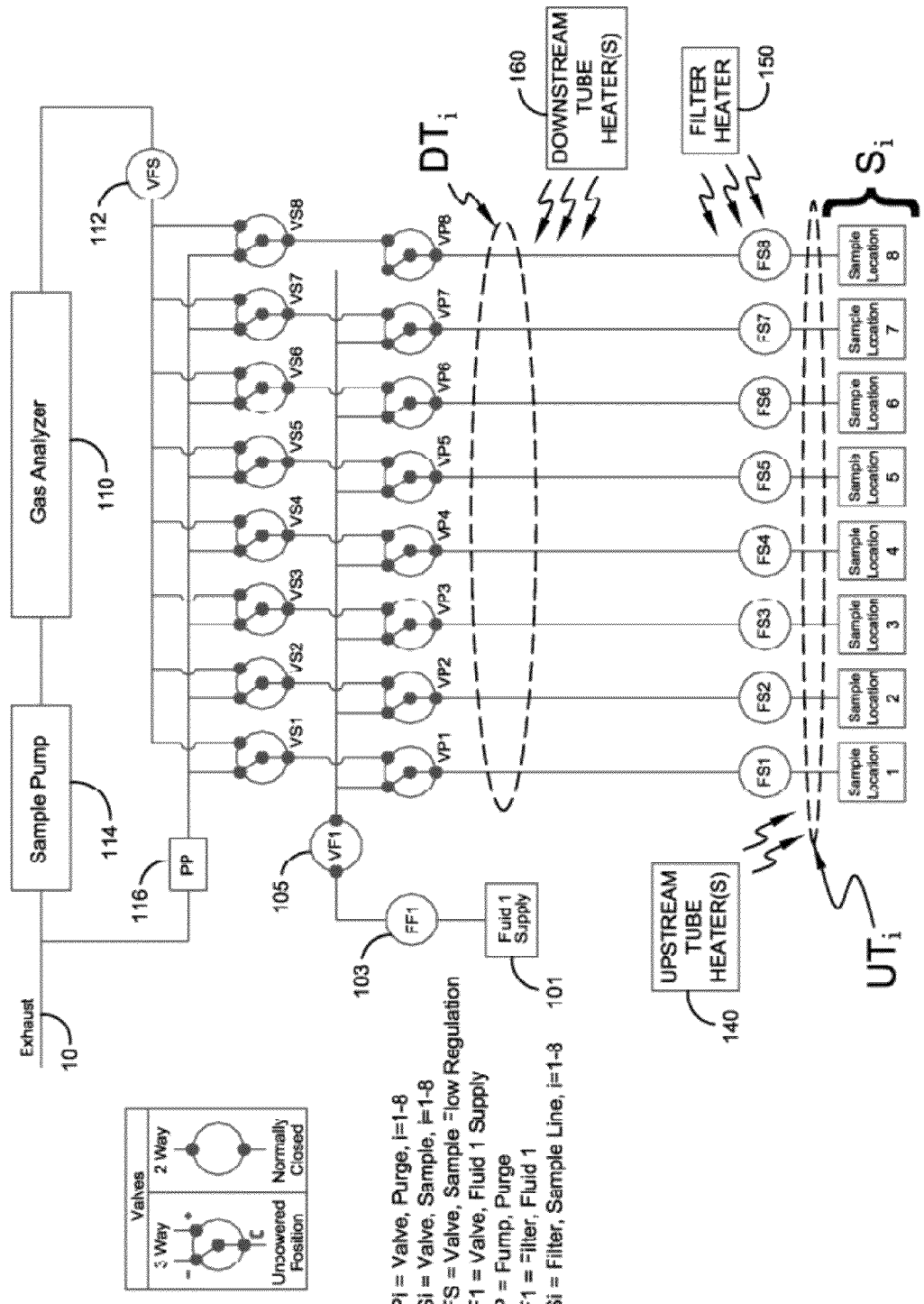
FIG. 1 is a block flow diagram illustration of prior art.

The novel sampling system in accordance with the present invention provides a remedy for the plugging that occurs in most moderate and severely complex fluids containing a mixture of particles, condensable and complex chemical reactions in a non-obvious, useful and cost-effective manner. In addition, extracted fluid properties undergo less change and more accurately represent the fluid being sampled. When complexity and contamination of the sampled fluids is only moderately severe (such as mixtures of reducing gases, dusts and soot found in heat treating furnaces and headspace of bioprocess reactors), the following two improvements can suffice:

1. Placing the sample filters FS1-FS8 far from the sampling location instead of in close proximity—the ratio of the fluid transport tube lengths LUi/LDi being much greater than 1 whereas in the prior art the ratio is much less than 1.0, and combined with use of specially selected filter media. This non-intuitive approach offers three distinct benefits:
   a. An increased percentage of the particulates and condensables are removed by settling or coating the inside of the fluid transport tube before the filter is reached resulting in longer filter life.
   b. Smaller filter surface area as well as "absolute" filter media, that more effectively removes smaller diameter particles, can be used and still have acceptable filter capacity
   c. When the fluid contains a mixture of liquids and vapors (gases) of the same chemical compound, filter media can often be selected that minimizes the passage the liquid phase and maximizes of its vapor (if placed near the sampling location, this type of filter would allow vapor to pass through that as it cools further might partially condense downstream of the filter and render reverse flow cleaning methods inoperative)
2. Use of small diameter fluid transport tubing T1 (0.125" inside diameter or less) to reduce the likelihood of plugging and use of high flow rate blow back gas. This non-intuitive approach offers seven distinct benefits:
   a. The sample transit time is rapid even at low flow rates
   b. Less mixing of the fluid sample occurs inside the fluid transport tube because smaller diameter flows are less likely to be turbulent and are more likely to approximate theoretical "plug flow" conditions (sharp transitions in fluid properties extracted from the sample location can thus be analyzed).
   c. Less mixing of fluids in the sample fluid transport tube also results in more effective removal of condensation and solid deposits during reverse flow of a fluid (either the sample fluid or a clean blow back fluid).
   d. Fluid sample temperature transitions are faster, better maintaining the sample integrity (especially when the fluid transport tubing is connected to a heat conducting fitting attached to an outside furnace or vessel wall or a line cooling system is also used).
   e. Faster fluid temperature transitions also result in less deposits of sample reaction or condensation products in the form of solids and liquids, and those that occur are nearer the sampling location and not as distributed along the sample fluid transport tube site.
   f. Chemical reactions and physical deposition that occurs in the sample fluid transport tube even in the absence of temperature effects are also located nearer the sampling location.
   g. Smaller fluid transport tubing is easier to install, lower cost and uses less fittings than larger diameter fluid transport tubing.

Figure 2:
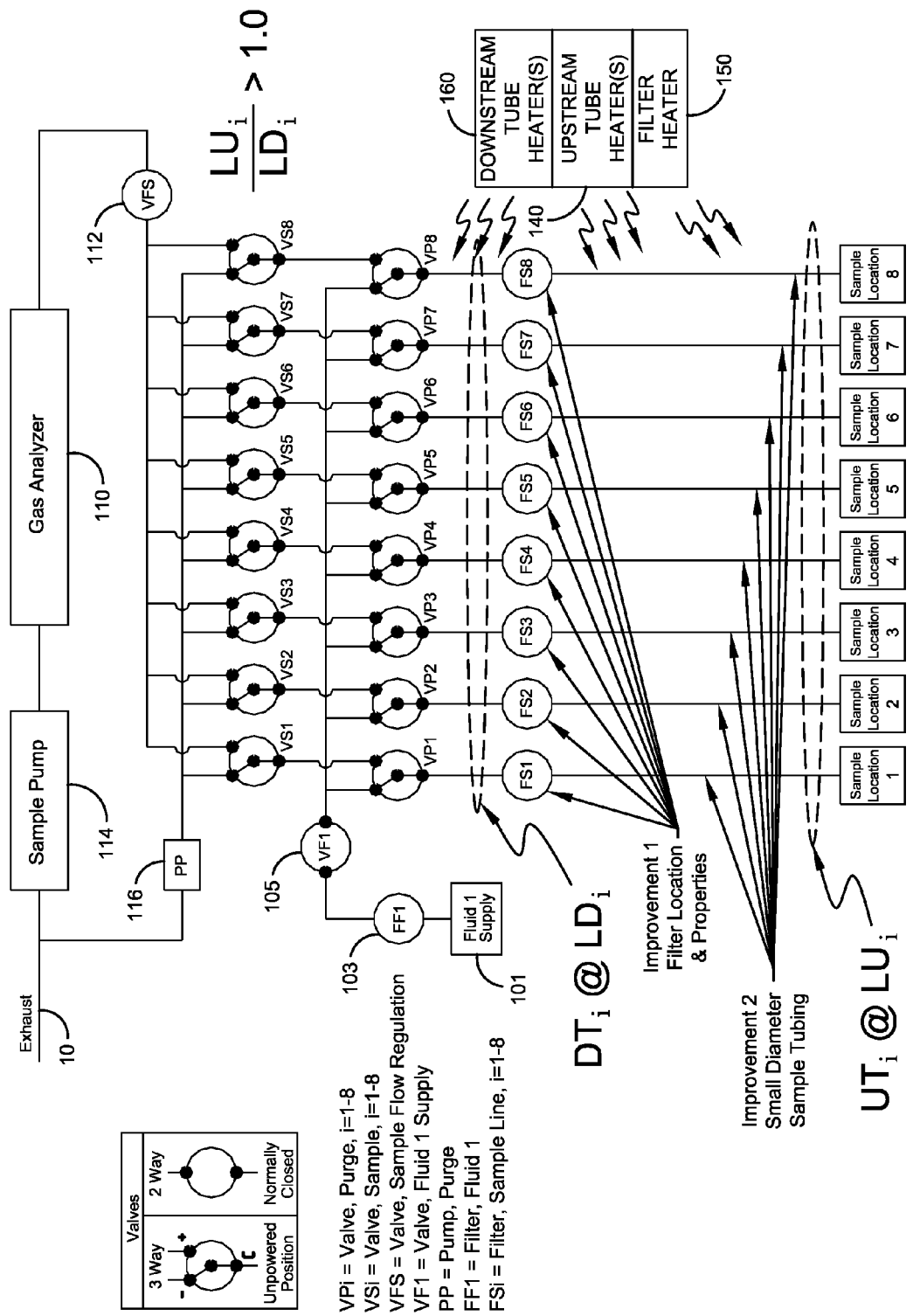
FIG. 2 is a block flow diagram of extractive fluid sampling system in accordance with the present invention.

FIG. 2 of the drawings presents a diagram of a chemical analyzer with the improved sampling system of the invention for measuring the chemical composition of heat treating furnace gases, some bioprocesses and other similar moderately contaminated fluids. A preferred embodiment includes a typical sampling system with these improvements and can also include heated sample line fluid transport tubing or gas dilution (both not shown). Typically Fluid 1 consists of elevated pressure clean and dried air or nitrogen that successfully dislodges accumulated sample particles and most condensates in these applications.

When complexity and contamination of the sampled fluids is severe (such as high temperature untreated coal combustion gases and reducing gases found in high temperature powdered metal annealing operations), the additional improvement in combination with the those disclosed in FIG. 2 can suffice.

Figure 3:
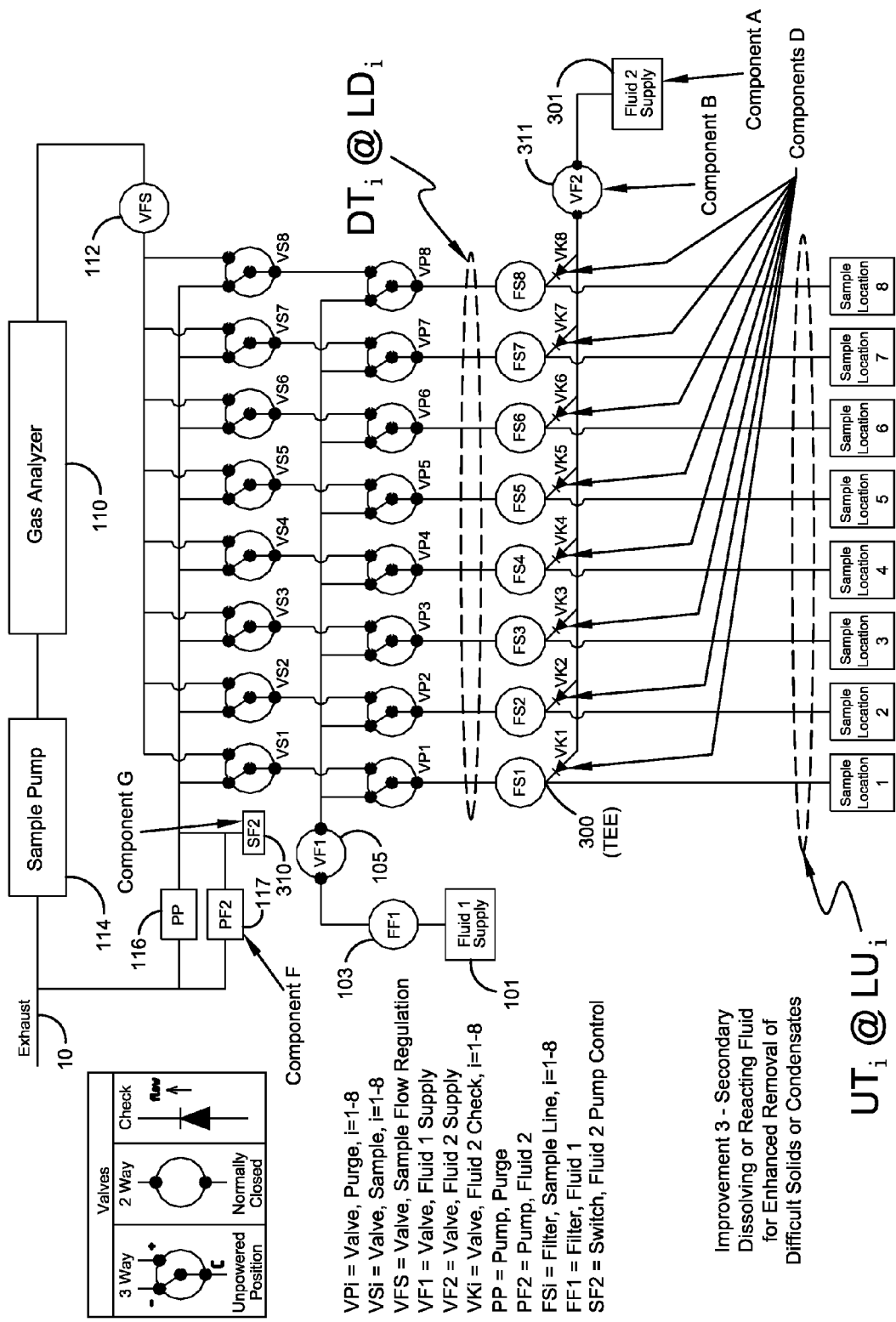
FIG. 3 is another block flow diagram of another extractive fluid sampling system in accordance with the present invention embodying the principles of the present presented in FIG. 2.

By referring to FIG. 3 of the drawings, an improvement can be seen by adding a specially designed second fluid supply and control system that dissolves or reacts with deposits in the sample fluid transport tube and on the surface of the filter media. This improvement would generally be activated less frequently than the non-reactive blow back fluid system and has a more complex configuration. Unlike the inert blow back fluid which is passes through the sample line filters in a reverse direction during operation, this second fluid does not pass through the filters. This fluid can flow only as far as the upstream side of the filter media (controlled by the media material itself when liquid or closed upstream valves when a gas or vapor) and preferably is controlled in such a way as to fully coat the upstream (sample location) side of the filter media. Either by supplied Fluid 2 pressure or activating Fluid 1 blow back following a Fluid 2 fill, Fluid 2 flows in a reverse direction from the point of entry through to the sample fluid transport tubing into the sample location. This non-intuitive additional system is composed of four to six components depending on configuration:

- h. A fluid supply system that can safely store or supply gas or liquid even if hazardous (Fluid Supply 2 on FIG. 3)—always included
- i. A control valve designed to handle either a pressurized supply (such as a supply of de-ionized water or a reactive gas from a pressurized pipe) or can allow a specialized supply pump to force or draw the fluid into the sampling system (VF2 on FIG. 3)—always included
- j. A manifold (or tubing with multiple "tees," i.e., a 3-port connection) connected to the control valve that leads to each sampling line (identified by numeral 300 in FIG. 3—one shown)—always included
- k. Individual check valves (VKi as shown in FIG. 3) or solenoid valves (not shown) that connect to the manifold located on individual sample line "tees" in close proximity to and on the sample location side of each sample line filter FSi designed to prevent the dissolving or reacting fluid from being drawn into the sample flow during analysis, minimize residual fluid 2 volume remaining in sample system after completion of it cleaning cycle and prevent Fluid 1 blow back from mixing with Fluid 2—always included
- l. The connection "tee" or other junction into each sample line (shown in FIG. 3 but not labeled)—always included
- m. A specialized supply pump if used (PF2 on FIG. 3)—included when Fluid 2 supply pressure is too low
- n. A pressure or flow switch (SF2 on FIG. 3)—included when a means of determining when the proper amount of Fluid 2 has been introduced The extractive fluid sampling system of the present invention may provide one or more of the following distinct benefits when removing complex sample line contamination:

- a. In most cases, Fluid 2 consists of a higher viscosity and density fluid (most often a liquid) than Fluid 1 (most often a gas) can and these properties provide better entraining of particles lodged on the filter media and on the sample tubing walls
- b. Most condensables can be dissolved by proper selection of Fluid 2 and once dissolved are more easily transported out of the sample system in solution
- c. Most solids that form from combinations of particles and condensables can also be dissolved by Fluid 2 if properly chosen and also transported out of the sample system in solution or as entrained particles that have less tendency to stick to the tubing or filter media
- d. When sampling high temperature processes, a liquid can be selected that changes phase and/or suddenly cools the hottest portion of the sample tubing resulting in either an even more effective cleaning of the area where most of the reacted solids form and/or sufficient sudden change in fluid transport tubing temperature that can result in dislodging of non-dissolving or reacting solids because of differential contraction of the sample fluid transport tubing and the solid coating it (thermal shock)
- e. In those cases where dissolving a solid or a condensing material does not work well, a liquid or gas can be selected that reacts solids in such a way that a more easily removed solid, liquid or gas is formed FIG. 3 presents a diagram of a chemical analyzer with the additionally improved sampling system for measuring the chemical composition of coal combustion gases, powdered metal annealing furnace gases, and other similar severely contaminated fluids. This system includes the second fluid that is used separately or in conjunction with the blow back fluid to enhance the removal of difficult to remove solids and liquids that form in the sampling fluid transport tubes and on the filter media and walls. While FIG. 3 discloses only one Fluid 2 system, use of additional fluids (3, 4, 5, etc.) installed in parallel with the Fluid 2 system are easily added and are desirable in certain situations. A preferred embodiment includes a sampling system with the FIG. 2 and FIG. 3 improvements and can also include heated sample line fluid transport tubing or gas dilution (both not shown).

A preferred embodiment for coal combustion gases would use de-ionized water as Fluid 2 with the possible addition of a vaporizing base mixed in (an example is ammonium hydroxide). This fluid has been shown to dissolve most inorganic acids present in the combustion products as well as most solids that can form a plug the sample fluid transport tubing. This system has successfully operated in a commercial electric power plant for a period in excess of six months. A preferred embodiment for a powdered metal annealing and decarburizing may include de-ionized water as Fluid 2 combined with hydrogen gas periodically added as a Fluid 3. In this case, addition of Fluid 3 can be in the same manner a Fluid 2 or simultaneously with or as an alternate to Fluid 1.

It will be apparent to those skilled in the art that various changes and modifications may be made without departing from the spirit of the invention. While the present invention has been particularly shown and described with reference to the accompanying figures, it will be understood, however, that other modifications thereto are of course possible, all of which are intended to be within the true spirit and scope of the present invention. It should be appreciated that components of the invention aforedescribed may be substituted for other

I claim:

1. An extractive fluid sampling system, comprising:
   at least one upstream sample fluid transport tube initiating at a sample location, for transporting a fluid sample from the sample location to at least one fluid filter;
   at least one fluid filter positioned far enough from the sample location sufficient to at least partially clean the fluid sample by settling or coating the transport tube with sample contaminants, to increase sample separation prior to contact with the at least one fluid filter and increase filter life;
   a fluid analyzer; and
   at least one downstream sample fluid transport tube, for transporting the cleaned fluid sample from the at least one fluid filter to the fluid analyzer;
   wherein the at least one upstream sample fluid transport tube includes a small inner diameter cross-section to reduce turbulent flow and reduce mixing.

2. The extractive fluid sampling system of claim 1, wherein the sample contaminants differ in phase from the fluid sample.

3. The extractive fluid sampling system of claim 1, further comprising a downstream reverse flow cleaning system, adapted to introduce a downstream cleaning fluid in a reverse sample flow direction to clean one or more of the at least one upstream sample fluid transport tube and at least one fluid filter.

4. The extractive fluid sampling system of claim 3, wherein the downstream reverse flow cleaning system comprises a downstream cleaning fluid supply, downstream cleaning fluid filter, downstream cleaning fluid control valve and downstream cleaning fluid transport tube.

5. The extractive fluid sampling system of claim 3, wherein the downstream cleaning fluid comprises clean and dried gas.

6. The extractive fluid sampling system of claim 3, wherein the downstream reverse flow cleaning system introduces the downstream cleaning fluid downstream of the at least one fluid filter.

7. The extractive fluid sampling system of claim 1, further comprising a sample pump for controlling the flow of fluid sample in the system.

8. The extractive fluid sampling system of claim 1, wherein the at least one upstream sample fluid transport tube is heated.

9. The extractive fluid sampling system of claim 1, further comprising one or more sample valves for controlling sample fluid flow.

10. The extractive fluid sampling system of claim 1, further comprising an upstream reverse flow cleaning system, adapted to introduce an upstream cleaning fluid in the at least one upstream sample fluid transport tube.

11. The extractive fluid sampling system of claim 10, wherein the upstream cleaning fluid contacts the at least one upstream sample fluid tube and the at least one fluid filter.

12. The extractive fluid sampling system of claim 10, wherein the upstream reverse flow cleaning system comprises an upstream cleaning fluid supply, an upstream cleaning fluid control valve and an upstream cleaning fluid transport tube.

13. The extractive fluid sampling system of claim 10, wherein the upstream cleaning fluid does not pass through the at least one fluid filter.

14. The extractive fluid sampling system of claim 10, wherein the upstream cleaning fluid dissolves or reacts with sample contaminants in the at least one upstream sample fluid transport tube, on a surface of the at least one fluid filter or both.

15. The extractive fluid sampling system of claim 10, wherein the upstream cleaning fluid comprises a higher viscosity and density as compared to the downstream cleaning fluid.

16. An extractive fluid sampling system, comprising:
    at least one upstream sample fluid transport tube initiating at a sample location, for transporting a fluid sample from the sample location to at least one fluid filter;
    at least one fluid filter positioned far enough from the sample location sufficient to at least partially clean the fluid sample by settling or coating the transport tube with sample contaminants, to increase sample separation prior to contact with the at least one fluid filter and increase filter life;
    a fluid analyzer;
    at least one downstream sample fluid transport tube, for transporting the cleaned fluid sample from the at least one fluid filter to the fluid analyzer; and
    an upstream reverse flow cleaning system, adapted to introduce an upstream cleaning fluid in the at least one upstream sample fluid transport tube;
    wherein the at least one upstream sample fluid transport tube includes a small inner diameter cross-section to reduce turbulent flow and reduce mixing and wherein the upstream cleaning fluid does not pass through the at least one fluid filter.

* * * * *